_US009258497B2_

United States Patent
Tsuji

(10) Patent No.: US 9,258,497 B2
(45) Date of Patent: Feb. 9, 2016

(54) CORRECTION IMAGE CREATION DEVICE, RADIOGRAPHIC IMAGING DEVICE, IMAGING DEVICE, COMPUTER READABLE MEDIUM AND CORRECTION IMAGE CREATION METHOD

(71) Applicant: FUJIFILM Corporation, Tokyo (JP)
(72) Inventor: Tetsuya Tsuji, Kanagawa (JP)
(73) Assignee: FUJIFILM Corporation, Tokyo (JP)
( * ) Notice: Subject to any disclaimer, the term of this patent is extended or adjusted under 35 U.S.C. 154(b) by 52 days.
(21) Appl. No.: 14/293,697
(22) Filed: Jun. 2, 2014
(65) Prior Publication Data

US 2014/0267837 A1 Sep. 18, 2014

Related U.S. Application Data

(63) Continuation of application No. PCT/JP2012/079303, filed on Nov. 12, 2012.

(30) Foreign Application Priority Data

Mar. 30, 2012 (JP) ................................. 2012-082557

(51) Int. Cl.
| | | |
|---|---|---|
| *H04N 5/30* | (2006.01) | |
| *H04N 5/357* | (2011.01) | |
| *H04N 5/369* | (2011.01) | |
| *G01T 1/164* | (2006.01) | |
| *G01T 1/20* | (2006.01) | |
| *G01T 1/17* | (2006.01) | |
| *A61B 6/00* | (2006.01) | |
| *G01N 23/04* | (2006.01) | |
| *H04N 5/32* | (2006.01) | |
| *G06T 5/00* | (2006.01) | |
| *G06T 5/40* | (2006.01) | |
| *G06F 19/00* | (2011.01) | |

(52) U.S. Cl.
CPC .............. *H04N 5/357* (2013.01); *A61B 6/4233* (2013.01); *A61B 6/4283* (2013.01); *A61B 6/44* (2013.01); *A61B 6/4464* (2013.01); *A61B 6/5258* (2013.01); *A61B 6/5264* (2013.01); *G01N 23/04* (2013.01); *G01T 1/1647* (2013.01); *G01T 1/17* (2013.01); *G01T 1/20* (2013.01); *G06T 5/002* (2013.01); *G06T 5/40* (2013.01); *H04N 5/32* (2013.01); *H04N 5/369* (2013.01); *G06F 19/321* (2013.01); *G06T 2207/20012* (2013.01)

(58) Field of Classification Search
CPC ... G01T 1/1642; G01T 1/2985; G01T 1/1648; G01T 1/208; G01T 1/171
See application file for complete search history.

(56) References Cited

U.S. PATENT DOCUMENTS

2010/0040199 A1 2/2010 Enomoto
2010/0277592 A1* 11/2010 Yokoyama ............ G01T 1/1647
348/162

FOREIGN PATENT DOCUMENTS

| | | | |
|---|---|---|---|
| JP | 2003-110943 | A | 4/2003 |
| JP | 2007-28026 | A | 2/2007 |
| JP | 2010-42150 | A | 2/2010 |

OTHER PUBLICATIONS

International Search Report, issued in PCT/JP2012/079303, dated Feb. 12, 2013.
Written Opinion of the International Search Authority, issued in PCT/JP2012/079303, dated Feb. 12, 2013.
Notice of Reasons for Rejection dated May 12, 2015, for Japanese Application No. 2012-082557 with a partial English translation.

* cited by examiner

*Primary Examiner* — David Porta
*Assistant Examiner* — Mamadou Faye
(74) *Attorney, Agent, or Firm* — Birch, Stewart, Kolasch & Birch, LLP

(57) ABSTRACT

A correction image creation device includes: an acquisition unit that acquires at least one original image, which is a basis when creating a correction image used in offset correction with respect to an image that has been obtained by imaging; a determination unit that determines whether or not noise from the exterior is superimposed on the original image; and a cancellation unit that cancels creation of the correction image in a case in which it has been determined by the determination unit that noise from the exterior is superimposed on the original image.

18 Claims, 14 Drawing Sheets

FIG.6

INITIAL INFORMATION
INPUT SCREEN

100

PLEASE INPUT NAME OF SUBJECT, IMAGING SITE,
IMAGING POSTURE, AND EXPOSURE CONDITIONS.

NAME
IMAGING SITE
IMAGING POSTURE
EXPOSURE
CONDITIONS   TUBE VOLTAGE
             TUBE CURRENT
         EXPOSURE DURATION ( FINISHED )

CORRECTION IMAGE CREATION DEVICE, RADIOGRAPHIC IMAGING DEVICE, IMAGING DEVICE, COMPUTER READABLE MEDIUM AND CORRECTION IMAGE CREATION METHOD

CROSS-REFERENCE TO RELATED APPLICATION

This application is a Continuation of PCT International Application No. PCT/JP2012/079303 filed on Nov. 12, 2012, which claims priority under 35 U.S.C. §119 (a) to Japanese Patent Application No. 2012-082557 filed on Mar. 30, 2012. Each of the above applications is hereby expressly incorporated by reference, in its entirety, into the present application.

TECHNICAL FIELD

The present invention pertains to a correction image creation device, a radiographic imaging device, an imaging device, a computer readable medium, and a correction image creation method, and particularly relates to a correction image creation device, a radiographic imaging device, an imaging device, a computer readable medium, and a correction image creation method that create a correction image for offset correction.

BACKGROUND ART

Conventionally, imaging devices such as television cameras are configured to use clamping to set the black level of the imaging result to a predetermined signal level. For example, CCD solid-state image sensors use sensor portions arranged in a matrix to photoelectrically convert incident light and sequentially transfer and output stored charges obtained as a result. CCD solid-state image sensors are configured in such a way that a partial region of an imaging surface comprising the sensor portions arranged in a matrix in this way is shielded from light to create an optical black region, and the optical black level can be detected by the output signal level of this optical black region. Because of this, imaging devices are configured to integrate the output signals of imaging elements obtained from the optical black region to obtain a predetermined evaluation value and offset the output signal levels of the imaging elements so that this evaluation value becomes a predetermined value, thereby forming a feedback loop to set the black level of the imaging result to a predetermined signal level.

However, in these imaging devices, when the signal level of the imaging result obtained from the optical black region momentarily changes due to noise getting mixed in, the evaluation value temporarily changes, and the black level needs to be corrected to correct this change.

Japanese Patent Application Laid-open (JP-A) No. 2003-110943 discloses a technology which, in an imaging device, detects an optical black level resulting from an output signal level of an optical black region in which a partial region of an imaging surface has been shielded from light and offsets the output signal level of an imaging element in accordance with the detection value. Specifically, the imaging device integrates, by frame, the luminance level obtained from the optical black region to detect an evaluation value representing the optical black level of the imaging result, uses this integrated value as a detection value resulting from detection data, offsets the luminance level of image data using a correction value based on this, and performs processing that clamps the black level of the imaging result to a predetermined signal level.

Furthermore, in recent years, digital imaging devices that use flat panel radiation detectors—or what are called flat panel detectors (FPDs)—having a phosphor and a large-area amorphous silicon sensor in close contact to directly digitalize a radiographic image without involving an optical system or the like have come into practical use. Furthermore, FPDs that use amorphous selenium, lead iodide ($PbI_2$), and mercury iodide ($HgI_2$), for example, to convert radiation into electrons and use a large-area amorphous silicon sensor to detect the electrons have similarly come into practical use. These FPDs show promise as next-generation digital imaging devices because in principle they are capable of capturing not only still images but also moving images.

The sensors used in FPDs comprise several million pixels, and the characteristics of the pixels differ from one another. The characteristics particularly important for image sensors are the dark current characteristic and the sensitivity characteristic. Therefore, in FPDs, offset correction for correcting these characteristics is implemented, and the sensors are used as sensors in which the characteristics of the pixels are substantially uniform.

SUMMARY OF INVENTION

Technical Problem

In the technology of JP-A No. 2003-110943, when acquiring the correction value for offset correction, in order to obtain a correction value from which noise has been removed and whose precision is high, unique functions become necessary, and in order to acquire that correction value, a certain amount of required time ends up being required. In imaging devices and radiographic imaging devices, a technique for easily creating a correction image with little noise for offset correction has been desired.

The present invention provides a correction image creation device, a radiographic imaging device, an imaging device, a computer readable medium, and a correction image creation method which, when creating a correction image for offset correction, can easily create a correction image with little noise while ensuring that a correction image having noise superimposed thereon is not created.

Solution to Problem

A correction image creation device of the present invention includes: an acquisition unit that acquires at least one original image, which is a basis when creating a correction image used in offset correction with respect to an image that has been obtained by imaging; a determination unit that determines whether or not noise, from an exterior, is superimposed on the original image; and a cancellation unit that cancels creation of the correction image in a case in which it has been determined by the determination unit that noise from exterior is superimposed on the original image.

According to this correction image creation device, at least one original image, which is a basis when creating a correction image used in offset correction with respect to an image that has been obtained by imaging is acquired by the acquisition unit, whether or not noise from the exterior is superimposed on the original image is determined by the determination unit, and creation of the correction image is cancelled by the cancellation unit in a case in which it has been determined by the determination unit that noise from the exterior is superimposed on the original image.

In this way, according to this correction image creation device, by cancelling creation of the correction image in a case in which noise from the exterior is superimposed on the original image, a situation where a correction image having noise superimposed thereon is created can be avoided, and, as a result, a correction image with little noise for offset correction can be easily created.

Furthermore, the correction image creation device of the present invention may be configured in such a way that, in a case in which it has been determined that noise from the exterior is superimposed on the original image, the cancellation unit cancels creation of the correction image using the original image on which the noise is superimposed. Because of this, a situation where an original image having noise superimposed thereon is used as an image for offset correction can be avoided.

Furthermore, the correction image creation device of the present invention may be configured to further include a creation unit that creates the correction image using an original image that has been determined by the determination unit as not having noise from the exterior superimposed on it. Because of this, a correction image with little noise can be created.

Furthermore, the correction image creation device of the present invention may be configured to acquire, as the original image, a radiographic image that has been captured by an imaging device, which irradiates a subject with radiation from a radiation source and uses a detector to detect radiation that has passed through the subject to thereby capture a radiographic image of the subject, without irradiating a subject with radiation from the radiation source. Because of this, a correction image with little noise for offset correction with respect to a radiographic image can be easily created.

Furthermore, the correction image creation device of the present invention may be configured in such a way that the acquisition unit acquires, as the original image, an image that has been captured by a solid-state image sensor without the presence of incident light. Because of this, a correction image with little noise for offset correction with respect to an image that has been captured by visible light imaging can be easily created.

Furthermore, the correction image creation device of the present invention may be configured in such a way that the noise is at least one of noise caused by scatter radiation, noise caused by an impact, and noise caused by electromagnetic waves. Because of this, a correction image with little noise for offset correction can be easily created.

Furthermore, the correction image creation device of the present invention may be configured in such a way that the determination unit determines whether or not noise caused by scatter radiation is superimposed by comparing, against a predetermined threshold value, mean values of pixel values in a plurality of regions in the original image. Because of this, noise caused by scatter radiation and superimposed on a correction image for offset correction can be easily detected.

Furthermore, the correction image creation device of the present invention may be configured in such a way that the determination unit determines whether or not noise caused by an impact is superimposed on the basis of numbers of pixels with respect to differences away from a reference value of a histogram represented by differences in pixel values of corresponding pixels in an image for offset correction that has already been created and an original image, differences in pixel values of corresponding pixels in original images, differences in pixel values of corresponding pixels in a difference image obtained from a plurality of original images on which noise is not superimposed and an original image, or differences in pixel values of corresponding pixels in a mean image of a plurality of original images on which noise is not superimposed and an original image, and numbers of pixels with respect to the differences. Because of this, noise caused by an impact and superimposed on a correction image for offset correction can be easily detected.

Furthermore, the correction image creation device of the present invention may be configured in such a way that the determination unit determines whether or not noise caused by electromagnetic waves is superimposed on the basis of the spread of a histogram represented by differences in pixel values of corresponding pixels in an image for offset correction that has already been created and an original image and numbers of pixels with respect to those differences. Because of this, noise caused by electromagnetic waves and superimposed on a correction image for offset correction can be easily detected.

Furthermore, the correction image creation device of the present invention may be configured in such a way that the determination unit uses, as the original image, an image obtained as a result of noise caused by defective pixels having been removed by a median filter from the original image. Because of this, noise superimposed on a correction image for offset correction can be detected with good precision.

A radiographic imaging device of the present invention includes: the correction image creation device of the present invention; and an imaging device that irradiates a subject with radiation from a radiation source and uses a detector to detect radiation that has passed through the subject to thereby capture a radiographic image of the subject.

Consequently, according to the radiographic imaging device of the present invention, the radiographic imaging device acts in the same way as the correction image creation device of the present invention, so like the correction image creation device of the present invention, when creating a correction image for offset correction, a correction image with little noise can be easily created while ensuring that a correction image having noise superimposed thereon is not created.

An imaging device of the present invention includes: the correction image creation device of the present invention; and an imaging device that has a solid-state image sensor.

Consequently, according to the imaging device of the present invention, the imaging device acts in the same way as the correction image creation device of the present invention, so like the correction image creation device of the present invention, when creating a correction image for offset correction, a correction image with little noise can be easily created while ensuring that a correction image having noise superimposed thereon is not created.

A program stored in a non-transitory computer readable medium of the present invention causes a computer to function as the correction image creation device of the present invention.

Consequently, according to the program of the present invention, the program acts in the same way as the offset image creation device of the present invention, so like the offset image creation device of the present invention, when creating a correction image for offset correction, a correction image with little noise can be easily created while ensuring that a correction image having noise superimposed thereon is not created.

An offset image creation method of the present invention includes: acquiring at least one original image, which is a basis when creating a correction image used in offset correction with respect to an image that has been obtained by imaging; determining whether or not noise from the exterior is superimposed on the original image; and cancelling creation of the correction image in a case in which it has been determined that noise from the exterior is superimposed on the original image.

According to the offset image creation method of the present invention, the offset image creation method acts in the same way as the offset image creation device of the present invention, so like the offset image creation device of the present invention, when creating a correction image for offset correction, a correction image with little noise can be easily created while ensuring that a correction image having noise superimposed thereon is not created.

Advantageous Effects of Invention

According to the present invention, when creating a correction image for offset correction, a correction image with little noise can be easily created while ensuring that a correction image having noise superimposed thereon is not created.

BRIEF DESCRIPTION OF DRAWINGS

FIG. 6 is a drawing showing an example of an initial information input screen in the imaging system pertaining to the embodiments;

FIG. 9A is a drawing showing a case where there is no impact noise;

FIG. 9B is a drawing showing a case where there is impact noise;

DESCRIPTION OF EMBODIMENTS

Embodiments of the present invention will be described in detail below with reference to the drawings.

First Embodiment

Figure 1:
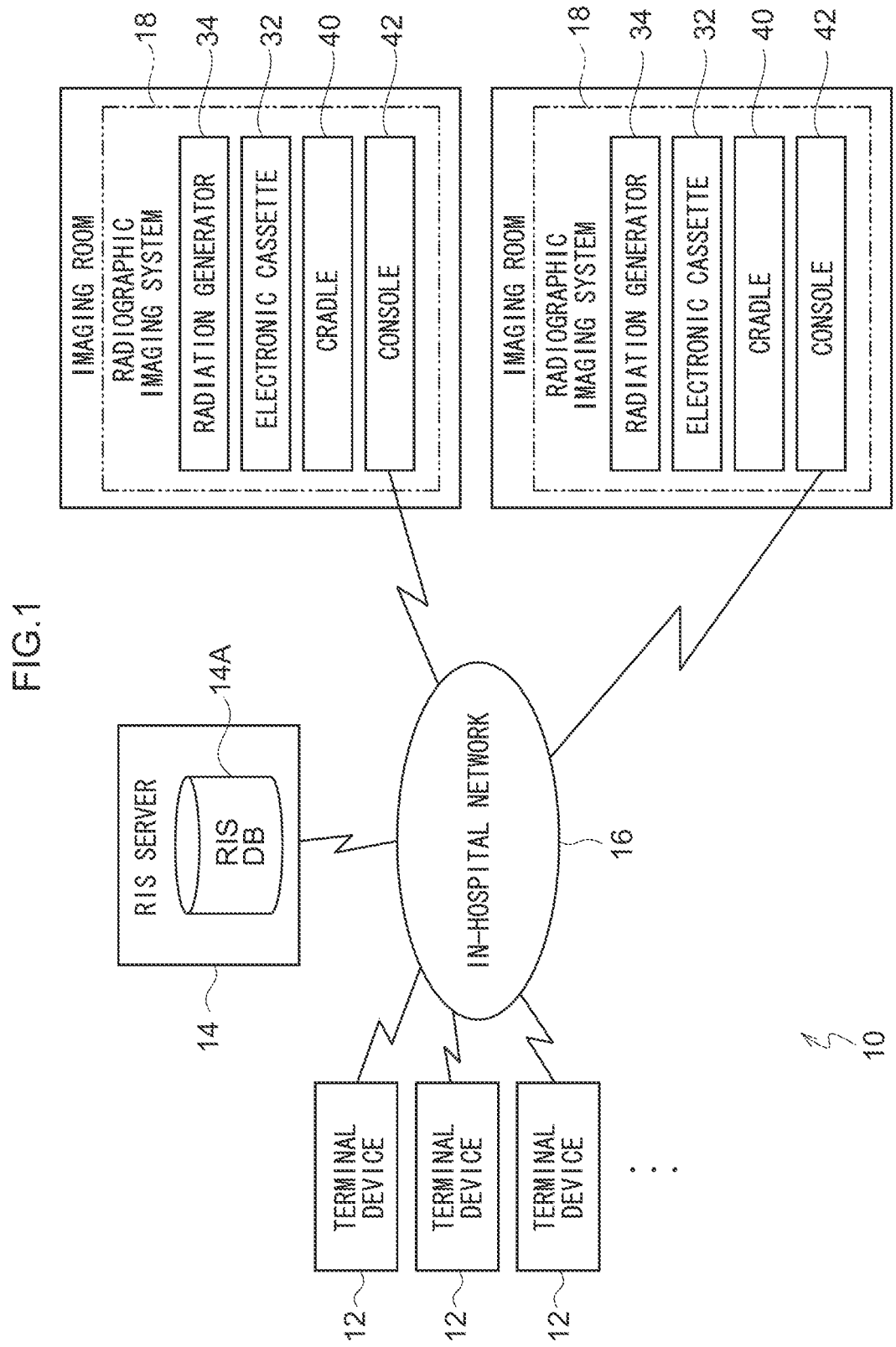
FIG. 1 is a block diagram showing the overall configuration of a system to which a radiographic imaging system pertaining to embodiments is applied.

FIG. 1 is a block diagram showing the overall configuration of a system 10 to which a radiographic imaging system 18 pertaining to a first embodiment is applied. First, the overall configuration of the system (hereinafter called a radiology information system, or "RIS") 10 to which the radiographic imaging system 18 pertaining to the first embodiment is applied will be described with reference to FIG. 1.

The RIS 10 is a system for managing information such as medical service appointments and diagnostic records in a radiology department and configures part of a hospital information system (hereinafter called an "HIS").

The RIS 10 has plural imaging request terminal devices (hereinafter called "terminal devices") 12, an RIS server 14, and the radiographic imaging system (hereinafter called an "imaging system") 18, which is installed in individual radiographic imaging rooms (or operating rooms) in a hospital, and these are connected to one another via an in-hospital network 16 comprising a wired or wireless local area network (LAN), for example. The RIS 10 configures part of the HIS disposed in the same hospital, and an HIS server (not shown in the drawings) that manages the entire HIS is also connected to the in-hospital network 16.

The terminal devices 12 are devices for doctors and radiologic technologists to input and browse diagnostic information and facility reservations, and radiographic imaging requests and imaging reservations are also made via the terminal devices 12. Each terminal device 12 is configured to include a display device and a personal computer, and the terminal devices 12 can communicate with one another via the RIS server 14 and the in-hospital network 16.

The RIS server 14 receives the imaging requests from each of the terminal devices 12 and manages radiographic imaging schedules in the imaging systems 18, and the RIS server 14 is configured to include a database 14A.

The database 14A is configured to include: information relating to patients (subjects), such as attribute information (names, sexes, dates of birth, ages, blood types, body weights, and patient identifications (IDs), etc.), medical histories, consultation histories, radiographic images captured in the past, etc.; information relating to later-described electronic cassettes 32 used in the imaging systems 18, such as identification numbers (ID information), models, sizes, sensitivities, imaging sites for which the cassettes can be used (details of imaging requests that the cassettes can accommodate), dates of first use, numbers of times used, etc.; and environment information representing the environments in which the radiographic images are captured using electronic cassettes 32, that is, the environments in which the electronic cassettes 32 are used (e.g., radiographic imaging rooms, operating rooms, etc.).

The imaging systems 18 capture radiographic images as a result of being operated by a doctor or a radiologic technologist in response to an instruction from the RIS server 14. Each imaging system 18 is equipped with: a radiation generator 34 that irradiates a subject with a dose of radiation X (see also FIG. 3) according to exposure conditions from a radiation source 130 (see also FIG. 2); an electronic cassette 32 that has a built-in radiation detector 60 (see also FIG. 3) that absorbs the radiation X that has passed through the imaging target site of the subject, generates charges, and produces image information representing a radiographic image on the basis of the generated charge quantity; a cradle 40 that charges a battery built into the electronic cassette 32; and a console 42 that controls the electronic cassette 32, the radiation generator 34, and the cradle 40.

The console 42 acquires various types of information included in the database 14A from the RIS server 14, stores the information in a later-described HDD 110 (see FIG. 4), and controls the electronic cassette 32, the radiation generator 34, and the cradle 40 on the basis of the information.

Figure 2:
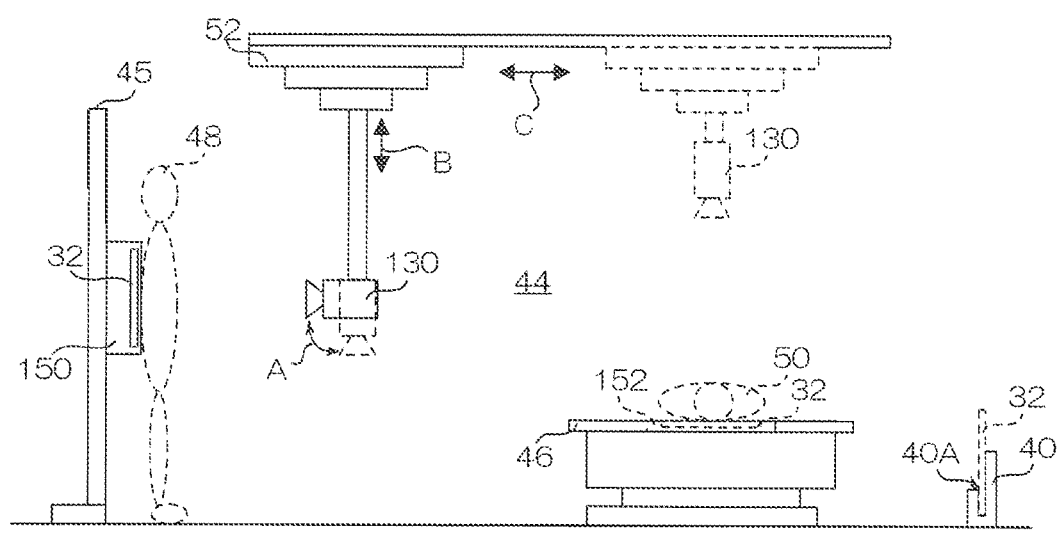
FIG. 2 is a drawing showing an example of the arrangement of devices, in a radiographic imaging room, of an imaging system pertaining to the embodiments.

FIG. 2 is a drawing showing an example of the arrangement of the devices, in a radiographic imaging room 44, of the imaging system 18 pertaining to the first embodiment. As shown in FIG. 2, a rack 45 used when performing radiographic imaging in an upright position and a bed 46 used when performing radiographic imaging in a recumbent position are installed in the radiographic imaging room 44. The space in front of the rack 45 serves as an imaging position 48 for a subject when performing radiographic imaging in the upright position, and the space above the bed 46 serves as an imaging position 50 for a subject when performing radiographic imaging in the recumbent position.

A holder 150 that holds the electronic cassette 32 is disposed on the rack 45, and the electronic cassette 32 is held in the holder 150 when performing radiographic imaging in the upright position. Likewise, a holder 152 that holds the electronic cassette 32 is disposed in the bed 46, and the electronic cassette 32 is held in the holder 152 when performing radiographic imaging in the recumbent position.

Furthermore, in order to enable both radiographic imaging in the upright position and radiographic imaging in the recumbent position using radiation from the single radiation source 130, a supporting and moving mechanism 52 that supports the radiation source 130 in such a way that the radiation source 130 is rotatable about a horizontal axis (the direction of arrow A in FIG. 2), is movable in the vertical direction (the direction of arrow B in FIG. 2), and is movable in the horizontal direction (the direction of arrow C in FIG. 2) is disposed in the radiographic imaging room 44. Here, the supporting and moving mechanism 52 is equipped with a drive source that rotates the radiation source 130 about the horizontal axis, a drive source that moves the radiation source 130 in the vertical direction, and a drive source that moves the radiation source 130 in the horizontal direction (none of the drive sources are shown in the drawings).

An accommodating portion 40A capable of storing the electronic cassette 32 is formed in the cradle 40.

When the electronic cassette 32 is not in use, the battery built into the electronic cassette 32 is charged by the cradle 40 in a state in which the electronic cassette 32 is stored in the accommodating portion 40A of the cradle 40, and when radiographic imaging is to be performed, the electronic cassette 32 is removed from the cradle 40 by a radiologic technologist, for example, and is held in the holder 150 of the rack 45 if the imaging posture is the upright position or is held in the holder 152 of the bed 46 if the imaging posture is the recumbent position.

Here, in the imaging system 18 pertaining to the present embodiment, various types of information are transmitted and received by wireless communication between the radiation generator 34 and the console 42 and between the electronic cassette 32 and the console 42.

The electronic cassette 32 can be used not only in radiographic imaging rooms and operating rooms but also during medical examinations and on hospital rounds because it is portable.

Figure 3:
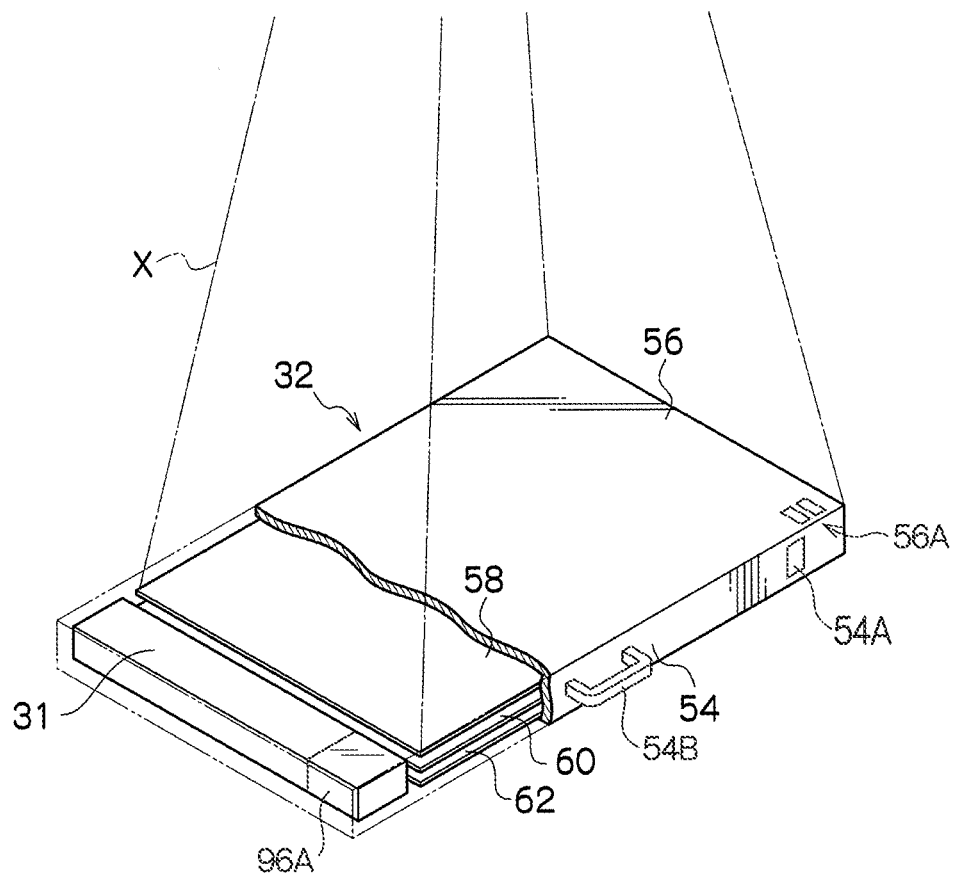
FIG. 3 is a drawing showing the internal configuration of an electronic cassette pertaining to the embodiments.

FIG. 3 is a drawing showing the internal configuration of the electronic cassette 32 pertaining to the first embodiment. As shown in FIG. 3, the electronic cassette 32 is equipped with a casing 54 comprising a material that allows the radiation X to pass through, and the electronic cassette 32 is given a waterproof and airtight structure. When the electronic cassette 32 is used in an operating room, for example, there is the concern that blood and/or various bacteria may adhere to the electronic cassette 32. Therefore, by giving the electronic cassette 32 a waterproof and airtight structure and sterilizing the electronic cassette 32 as needed, one electronic cassette 32 can be used repeatedly.

Inside the electronic cassette 54, a grid 58 that removes scatter radiation of the radiation X scattered by the subject, a radiation detector 60 that detects the radiation X that has passed through the subject, and a lead plate 62 that absorbs backscatter radiation of the radiation X are disposed in this order from an irradiated surface 56 side of the casing 54 that is irradiated with the radiation X. The irradiated surface 56 of the casing 54 may also be configured as the grid 58.

A case 31 that accommodates electronic circuits including a microcomputer and a rechargeable and removable battery 96A is disposed on one end side of the inside of the casing 54. The radiation detector 60 and the electronic circuits run on power supplied from the battery 96A disposed in the case 31. In order to avoid damage to the various circuits accommodated inside the case 31 in accompaniment with irradiation with the radiation X, it is preferred that a lead plate or the like be disposed on the irradiated surface 56 side of the case 31. The electronic cassette 32 pertaining to the present embodiment is a cuboid in which the shape of the irradiated surface 56 is rectangular, and the case 31 is disposed on one end portion in the long-dimension direction thereof.

Furthermore, a power switch 54A and an indicator 56A that indicates whether the power switch 54A is switched on or off (power state), operating modes such as "ready" and "transmitting data", and the operating state of the electronic cassette 32 such as the capacity remaining in the battery 96A are disposed in predetermined positions on outer walls of the casing 54. In the electronic cassette 32 pertaining to the present embodiment, a light emitting diode is applied as the indicator 56A, but the indicator is not limited to this and may also be configured by other indicating means such as a light emitting element other than a light emitting diode, a liquid crystal display, or an organic EL display.

Moreover, a handle 54B that is gripped when moving the electronic cassette 32 is disposed in a predetermined position on an outer wall of the casing 54. In the electronic cassette 32 pertaining to the present embodiment, the handle 54B is disposed in the center of a side wall disposed extending in the long-dimension direction of the irradiated surface 56 of the casing 54, but the place where the handle 54B is disposed is not limited to this, and it goes without saying that the handle 54B may also be disposed in another position, such as the center of a side wall disposed extending in the short-dimension direction of the irradiated surface 56 or a position offset from the centers of these side walls by a distance that takes into consideration lopsidedness in the position of the center of gravity of the electronic cassette 32.

Figure 4:
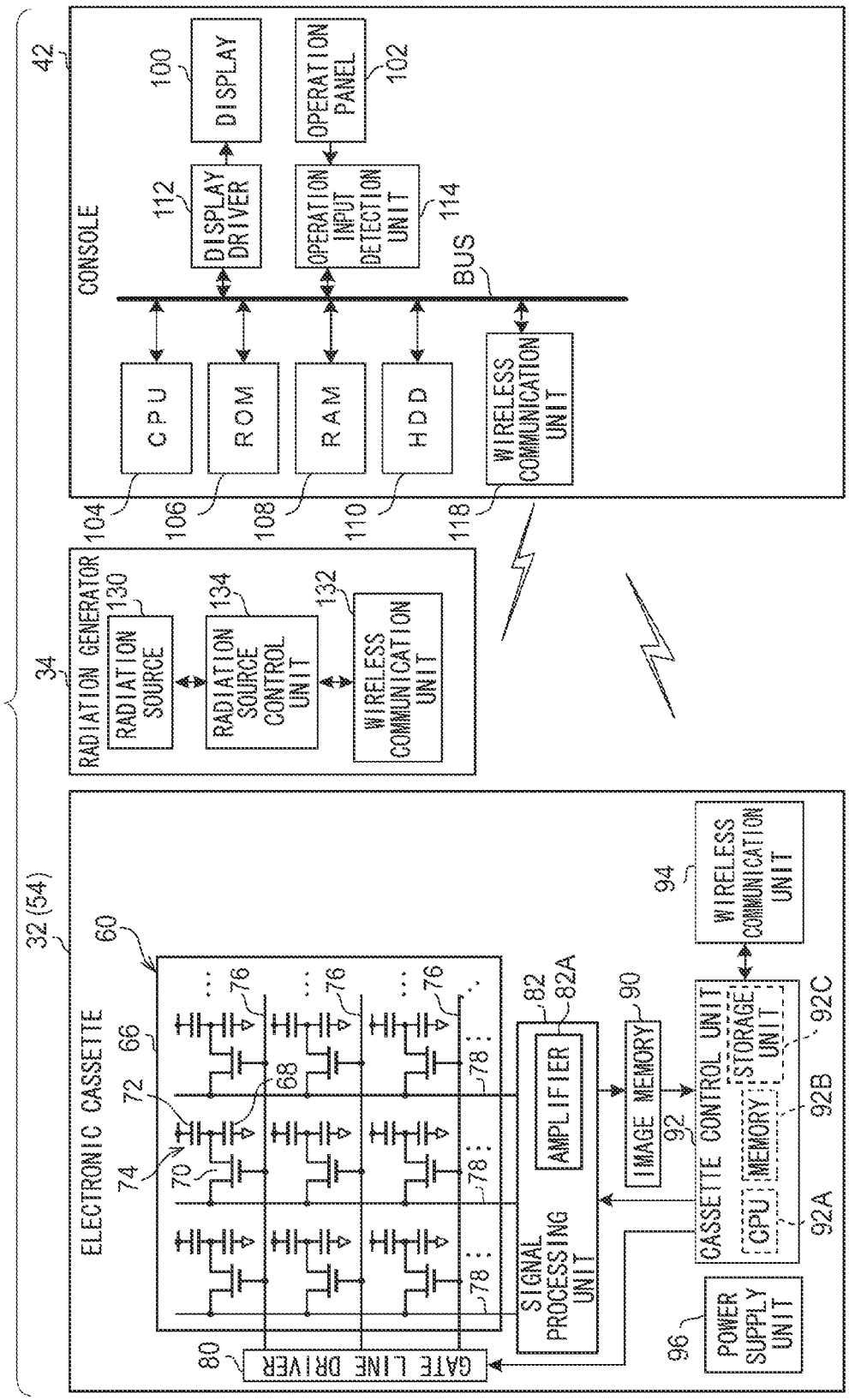
FIG. 4 is a block diagram showing the configurations of relevant parts of an electrical system of the imaging system pertaining to the embodiments.

Next, the configurations of relevant parts of an electrical system of the imaging system 18 pertaining to the first embodiment will be described with reference to FIG. 4. FIG. 4 is a block diagram showing the configurations of relevant parts of the electrical system of the imaging system 18 pertaining to the first embodiment.

As shown in FIG. 4, the radiation detector 60 built into the electronic cassette 32 is configured as a result of photoelectric conversion layer that absorbs the radiation X and converts the radiation X into charges being layered on a TFT active matrix substrate 66. The photoelectric conversion layer comprises amorphous selenium (a-Se) whose main component is selenium (e.g., having a content percentage of 50% or more), and when the photoelectric conversion layer is irradiated with the radiation X, it converts the radiation X with which it was irradiated into charges by internally generating charges (electron-hole pairs) of charge quantities corresponding to the dose of radiation with which it was irradiated. Instead of using a radiation-to-charge conversion material like amorphous selenium that directly converts the radiation X into charges, the radiation detector 60 may also use a phosphor material and a photoelectric conversion element (photodiode) to indirectly convert the radiation X into charges. Gadolinium oxysulfate (GOS) and cesium iodide (CsI) are well known as phosphor materials. In this case, the phosphor material converts the radiation X into light, and the photodiode that is the photoelectric conversion element converts the light into charges. Furthermore, as the photoelectric conversion element, an element using an organic photoelectric conversion material may be applied. Moreover, as the cesium iodide, CsI (TI), for example, may be applied.

Furthermore, numerous pixel portions 74 (in FIG. 4, the portions of the photoelectric conversion layer corresponding to the individual pixel portions 74 are schematically shown as photoelectric conversion portions 72) equipped with storage capacitors 68 that store the charges generated in the photoelectric conversion layer and TFTs 70 for reading out the charges stored in the storage capacitors 68 are arranged in a matrix on the TFT active matrix substrate 66, and the charges generated in the photoelectric conversion layer in accompaniment with the irradiation of the electronic cassette 32 with the radiation X are stored in the storage capacitors 68 of the individual pixel portions 74. Because of this, image information carried in the radiation X with which the electronic cassette 32 has been irradiated is converted into charge information and held in the radiation detector 60.

Furthermore, plural gate lines 76, which are disposed extending in one direction (a scan line direction; hereafter also called a "row direction") and are for switching on and off the TFTs 70 of the individual pixel portions 74, and plural data lines 78, which are disposed extending in a direction (a signal line direction; hereinafter also called a "column direction") intersecting the gate lines 76 and are for reading out the stored charges from the storage capacitors 68 via the TFTs 70 that have been switched on, are disposed on the TFT active matrix substrate 66. The individual gate lines 76 are connected to a gate line driver 80, and the individual data lines 78 are connected to a signal processing unit 82. When the charges are stored in the storage capacitors 68 of the individual pixel portions 74, the TFTs 70 of the individual pixel portions 74 are sequentially switched on by row by signals supplied via the gate lines 76 from the gate line driver 80, and the charges stored in the storage capacitors 68 of the pixel portions 74 whose TFTs 70 have been switched on are transmitted through the data lines 78 as analog electrical signals and are input to the signal processing unit 82. Consequently, the charges stored in the storage capacitors 68 of the individual pixel portions 74 are sequentially read out by row.

The electronic cassette 32 may be configured by a penetration side sampling (PSS) where the photoelectric conversion layer and the TFT active matrix substrate 66 are layered in this order from the side irradiated with the radiation X, or may be configured by a irradiation side sampling (ISS) where the TFT active matrix substrate 66 and the photoelectric conversion layer are layered in this order from the side irradiated with the radiation X.

The signal processing unit 82 is equipped with amplifiers and sample-and-hold circuits that are disposed for each of the individual data lines 78, and the charge signals transmitted through the individual data lines 78 are amplified by the amplifiers and are thereafter held in the sample-and-hold circuits. Furthermore, a multiplexer and an analog-to-digital (A/D) converter are sequentially connected to the output sides of the sample-and-hold circuits, and the charge signals held in the individual sample-and-hold circuits are sequentially (serially) input to the multiplexer and are converted into digital image data by the A/D converter.

An image memory 90 is connected to the signal processing unit 82, and the image data output from the A/D converter of the signal processing unit 82 are sequentially stored in the image memory 90. The image memory 90 has a storage capacity capable of storing plural frames' worth of image data, and each time radiographic imaging is performed, the image data that have been obtained by the imaging are sequentially stored in the image memory 90.

The image memory 90 is connected to a cassette control unit 92 that controls the operation of the entire electronic cassette 32. The cassette control unit 92 is configured to include a microcomputer and is equipped with a central processing unit (CPU) 92A, a memory 92B that includes a read-only memory (ROM) and a random access memory (RAM), and a nonvolatile storage unit 92C that comprises a hard disk drive (HDD) or a flash memory.

Moreover, a wireless communication unit 94 is connected to the cassette control unit 92. The wireless communication unit 94 pertaining to the present embodiment is compatible with a wireless local area network (LAN) standard typified by IEEE (Institute of Electrical and Electronics Engineers) 802.11a/b/g, for example, and controls the transmission of various types of information between the electronic cassette 32 and external devices by wireless communication. The cassette control unit 92 can wirelessly communicate with the console 42, and can transmit and receive various types of information to and from the console 42, via the wireless communication unit 94.

Furthermore, a power supply unit 96 is disposed in the electronic cassette 32, and the various circuits and elements described above (the gate line driver 80, the signal processing unit 82, the image memory 90, the wireless communication unit 94, the cassette control unit 92, etc.) run on power supplied from the power supply unit 96. The power supply unit 96 has the aforementioned built-in battery (secondary battery) 96A so as to not impair the portability of the electronic cassette 32, and the power supply unit 96 supplies power to the various circuits and elements from the charged battery 96A. In FIG. 4, illustration of wires connecting the various circuits and elements to the power supply unit 96 is omitted.

The console 42 is configured as a server computer and is equipped with a display 100, which displays operation menus and captured radiographic images, and an operation panel 102, which is configured to include plural keys and to which various types of information and operation instructions are input.

Furthermore, the console 42 pertaining to the present embodiment is equipped with a CPU 104 that controls the operation of the entire device, a ROM 106 in which various programs including a control program are stored beforehand, a RAM 108 that temporarily stores various types of data, a HDD 110 that stores and holds various types of data, a display driver 112 that controls the display of various types of information on the display 100, and an operation input detection unit 114 that detects states of operation with respect to the operation panel 102. Furthermore, the console 42 is equipped with a wireless communication unit 118 that transmits and receives various types of information such as later-described exposure conditions to and from the radiation generator 34 by wireless communication and also transmits and receives various types of information such as image data to and from the electronic cassette 32 by wireless communication.

The CPU 104, the ROM 106, the RAM 108, the HDD 110, the display driver 112, the operation input detection unit 114, and the wireless communication unit 118 are connected to one another via a system bus BUS. Consequently, the CPU 104 can access the ROM 106, the RAM 108, and the HDD 110, can control the display of various types of information on the display 110 via the display driver 112, and can control the transmission and reception of various types of information to and from the radiation generator 34 and the electronic cassette 32 via the wireless communication unit 118. Furthermore, the CPU 104 can grasp states of operation by a user with respect to the operation panel 102 via the operation input detection unit 114.

The radiation generator 34 is equipped with the radiation source 130, a wireless communication unit 132 that transmits and receives various types of information such as the exposure conditions to and from the console 42, and a radiation source control unit 134 that controls the radiation source 130 on the basis of the received exposure conditions.

The radiation source control unit 134 is also configured to include a microcomputer and stores the received exposure conditions and so forth. The exposure conditions received from the console 42 include information such as tube voltage, tube current, and exposure duration. The radiation source control unit 134 causes the radiation X to be emitted from the radiation source 130 on the basis of the received exposure conditions.

Next, a flow of imaging control processing in the imaging system 18 pertaining to the first embodiment will be described.

Figure 5:
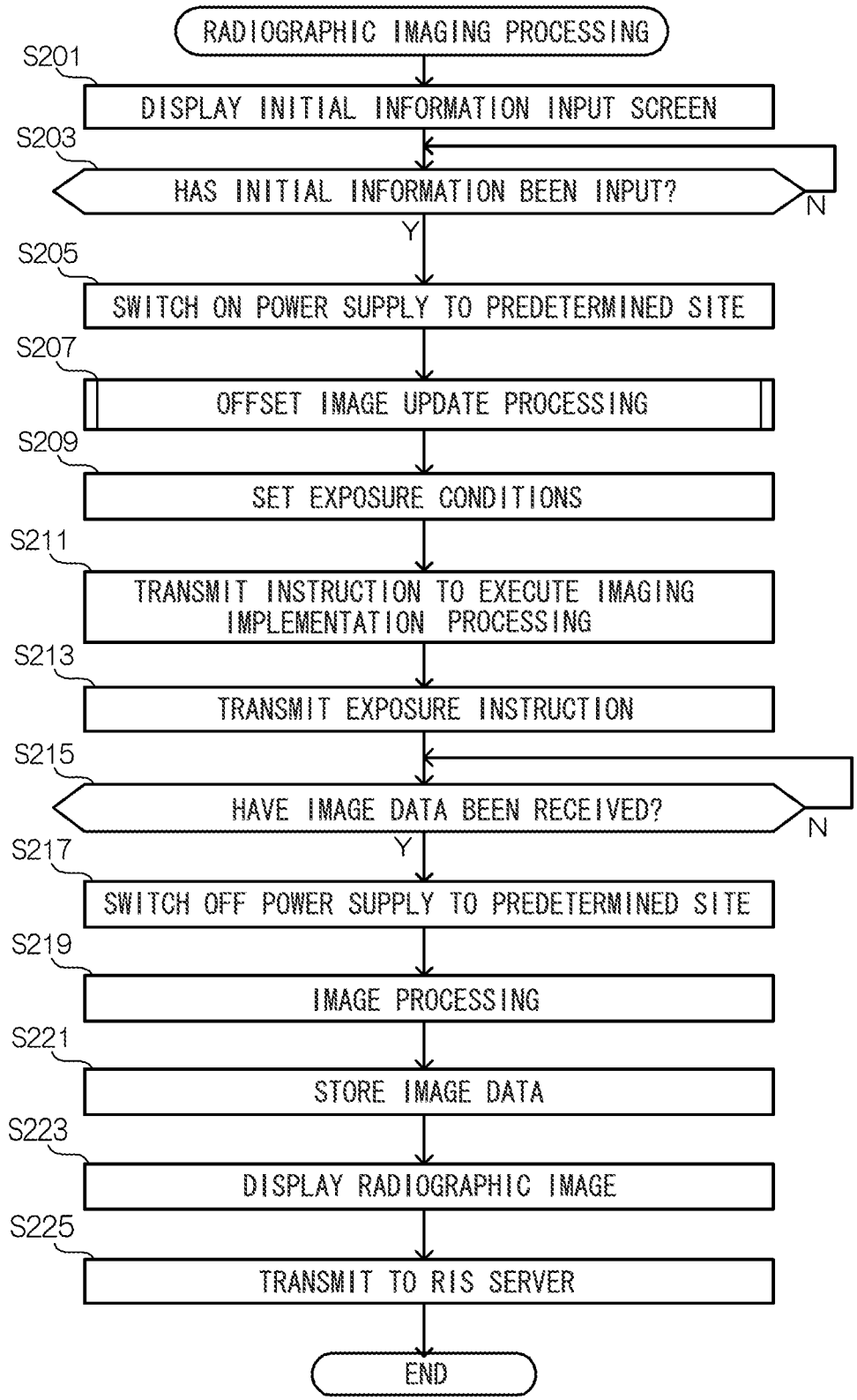
FIG. 5 is a flowchart showing a flow of imaging control processing in the imaging system pertaining to the embodiments.

FIG. 5 is a flowchart showing a flow of the imaging control processing in the imaging system 18 pertaining to the first embodiment. The imaging control processing is executed by the CPU 104 of the console 42 when performing radiographic imaging, and a program for performing the imaging control processing is stored beforehand in a predetermined region of the ROM 106.

In step S201, the CPU 104 controls the display driver 112 to cause the display 100 to display a predetermined initial information input screen.

FIG. 6 is a drawing showing an example of the initial information input screen in the imaging system 18 pertaining to the first embodiment. As shown in FIG. 6, displayed on the initial information input screen are a message prompting the radiographer to input information relating to various items, such as the name of the subject on which radiographic imaging is about to be performed, the imaging site, the posture during imaging (in the present embodiment, the recumbent position or the upright position), and the exposure conditions for exposure to the radiation X during imaging (in the present embodiment, the tube voltage, the tube current, and the exposure duration when exposing the subject to the radiation X), input fields for inputting these pieces of initial information, and a "finished" button indicating that the radiographer has finished inputting the information. The radiographer selects the "finished" button after inputting the initial information relating to the various items via the operation panel 102 in accordance with the initial information input screen.

In step S203, the CPU 104 determines whether or not the input of the initial information has been completed. At this time, the CPU 104 determines that the input of the initial information has been completed in a case where, for example, the "finished" button on the initial information input screen has been selected.

In a case where it has been determined in step S203 that the input of the initial information has been completed, in step S205 the CPU 104 estimates, on the basis of the initial information that has been input, the point in time at which exposure to the radiation X will end (hereinafter called "the point in time at which exposure will end") whose reference is the point in time at which charge storage is started by the radiation detector 60.

In the imaging system 18 pertaining to the present embodiment, the CPU 104 estimates the point in time at which exposure will end by adding the exposure duration that was input in the initial information input screen to a time period from when charge storage by the radiation detector 60 is started to until exposure to the radiation X is actually started, which is determined beforehand by the point in time at which charge storage by the radiation detector 60 is started in accordance with the processing of later-described step 211 in the electronic cassette 32 and a time period from the point in time at which the start of exposure to the radiation X has been instructed by the processing of later-described step 213 in the radiation generator 34 to until exposure is actually started.

Next, in step S207, the CPU 104 executes offset image update processing that produces image data (hereinafter called "offset image data") for correcting image data (hereinafter called "subject image data") that have been obtained by radiographic imaging by the radiation detector 60, by causing imaging by the radiation detector 60 to be executed in the same charge storage time period as the applied charge storage time period without causing radiation to be generated from the radiation generator 34.

Figure 7:
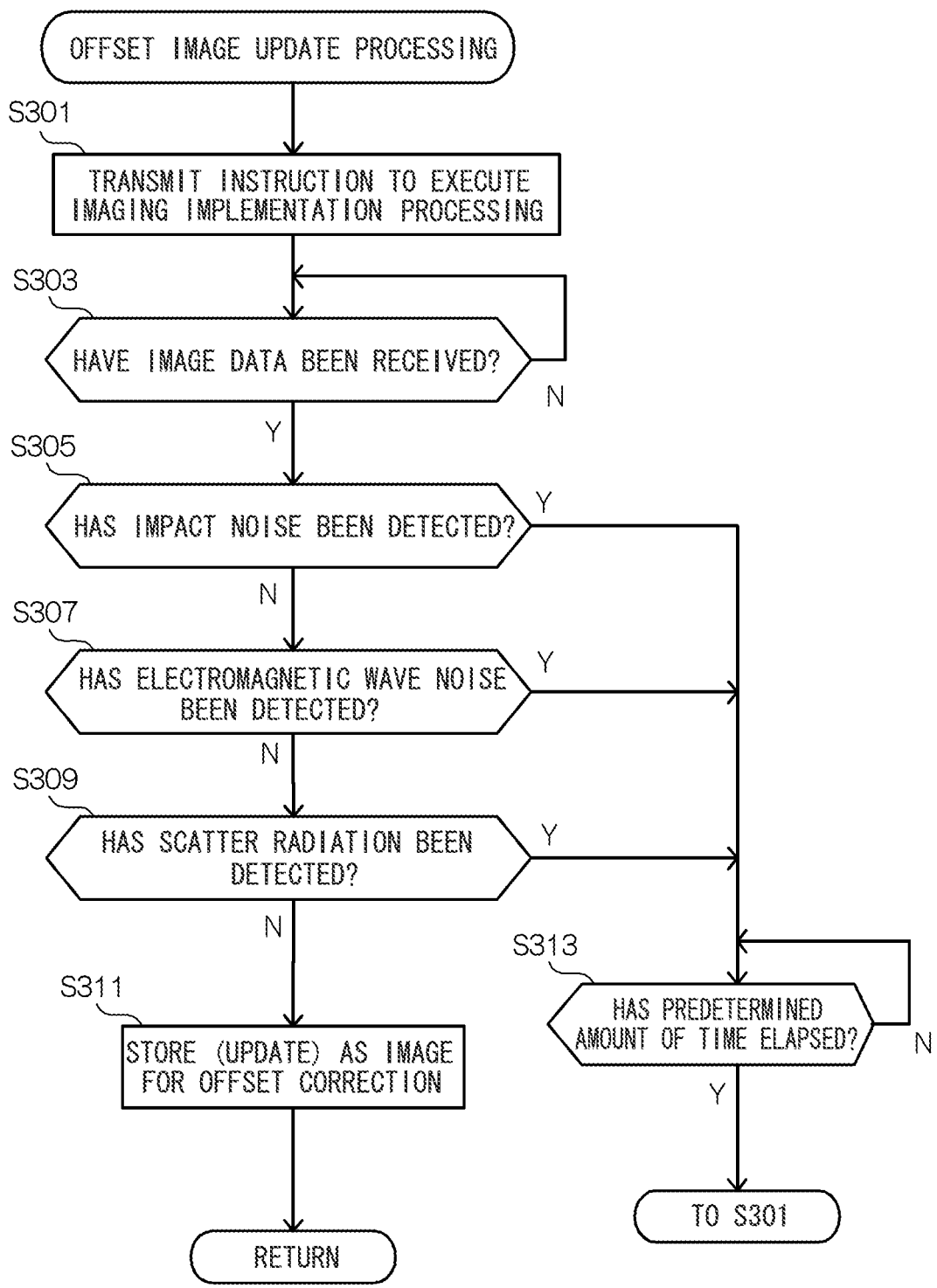
FIG. 7 is a flowchart showing a flow of offset image update processing in the imaging system pertaining to a first embodiment.

FIG. 7 is a flowchart showing a flow of the offset image update processing in the imaging system 18 pertaining to the first embodiment. The offset image update processing is executed by the CPU 104 of the console 42, and a program for performing the offset image update processing is stored beforehand in a predetermined region of the ROM 106.

In step S301, the CPU 104 transmits, to the electronic cassette 32 via the wireless communication unit 118, and together with information representing the applied charge storage time period and information representing the number of times imaging is to be performed (in the present embodiment, four times), instruction information instructing the electronic cassette 32 to execute imaging implementation processing in order to acquire an original image, which is a basis when creating a correction image used in offset correction. In response to this, the electronic cassette 32 performs a reset operation that discharges the charges being stored in the radiation detector 60 at this point in time, thereafter performs, a number of times equal to the designated number of times, imaging by the radiation detector 60 in the received applied charge storage time period, and transmits the image data that have been obtained thereby to the console 42 via the wireless communication unit 94.

Therefore, in step S303, the CPU 104 determines whether or not it has received the image data via the wireless communication unit 118 from the electronic cassette 32. At this time, the CPU 104 determines that it has received the image data in a case where it has received image data representing plural images that have been obtained by performing imaging a number of times equal to the designated number of times.

In a case where it has been determined in step S303 that the CPU 104 has received the image data, the CPU 104 determines, in regard to each of the images represented by the received image data, whether or not there are various types of noise in those images (images for creating an image for offset correction). In the first embodiment, the CPU 104 determines whether or not there is impact noise, electromagnetic wave noise, and scatter radiation noise in regard to each of the images.

Impact noise is noise that occurs when the portable electronic cassette 32 falls or collides with an object such as an obstacle and vibration is imparted to the electronic cassette 32. Electromagnetic wave noise is noise that occurs because of electromagnetic waves generated from another device such as a personal computer (PC) disposed in the neighborhood of the electronic cassette 32. Furthermore, scatter radiation noise is noise which, in a case where in addition to the radiation generator 34 another radiation generator that generates radiation such as X-rays is disposed in the neighborhood of the electronic cassette 32, occurs as a result of scatter radiation from the radiation generated by that other radiation generator being made incident on the electronic cassette 32.

Figure 8A:
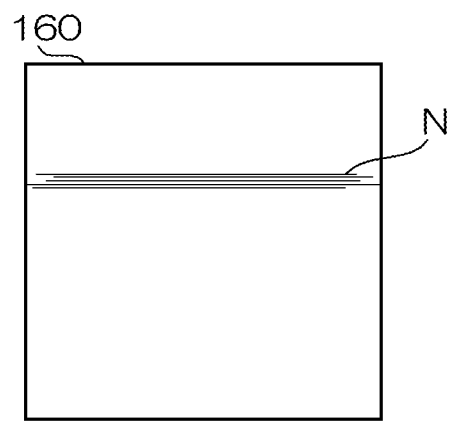
FIG. 8A is a schematic drawing showing an example of an image in which there is impact noise in the imaging system pertaining to the first embodiment.
Figure 8B:
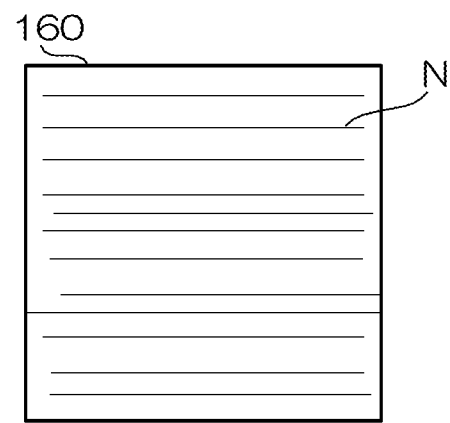
FIG. 8B is a schematic drawing showing an example of an image in which there is electromagnetic wave noise in the imaging system pertaining to the first embodiment.

FIG. 8A is a schematic drawing showing an example of an image in which there is impact noise in the imaging system 18 pertaining to the first embodiment, and FIG. 8B is a schematic drawing showing an example of an image in which there is electromagnetic wave noise in the imaging system 18 pertaining to the first embodiment. As shown in FIG. 8A, in a case where there is impact noise in an image 160 that has been captured by the electronic cassette 32, for example, linear noise N temporarily occurs in part of the image 160 (a region corresponding to lines from which signals were read by the signal processing unit 82 at the moment when the impact occurred in the electronic cassette 32). Furthermore, as shown in FIG. 8B, in a case where there is electromagnetic wave noise in an image 160 that has been captured by the electronic cassette 32, linear noise N temporarily occurs in the entire image 160.

First, in step S305, the CPU 104 determines whether or not impact noise has been detected from the received image data.

Figure 9A:
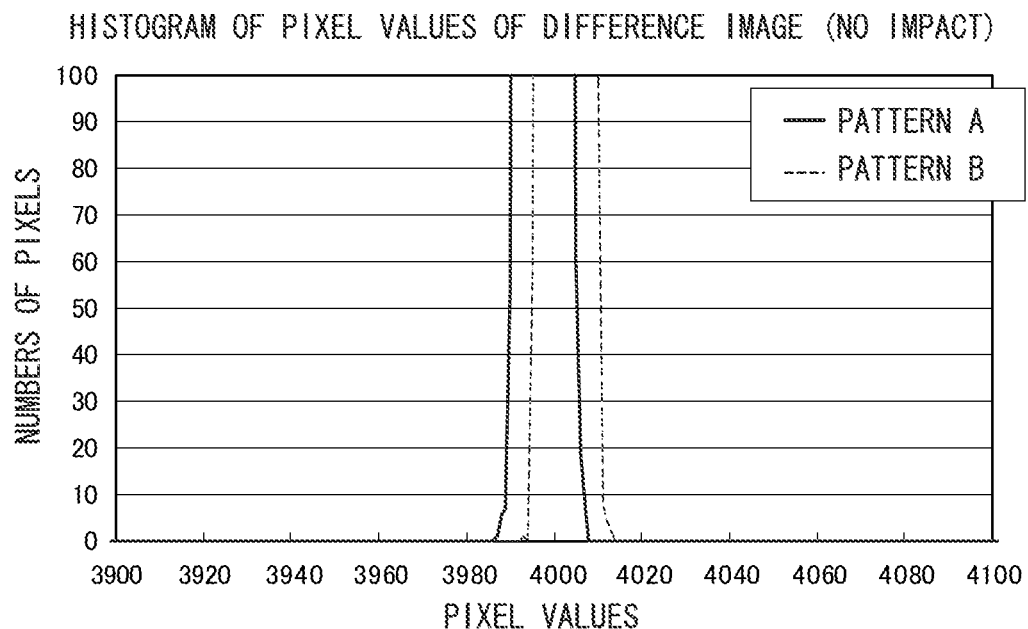
FIG. 9A and FIG. 9B are histograms showing pixel values of pixels in a difference image of an image captured the previous time and an image captured this time in the imaging system pertaining to the embodiments, with the horizontal axes representing pixel values (QL values) and the vertical axes representing numbers of pixels.
Figure 9B:
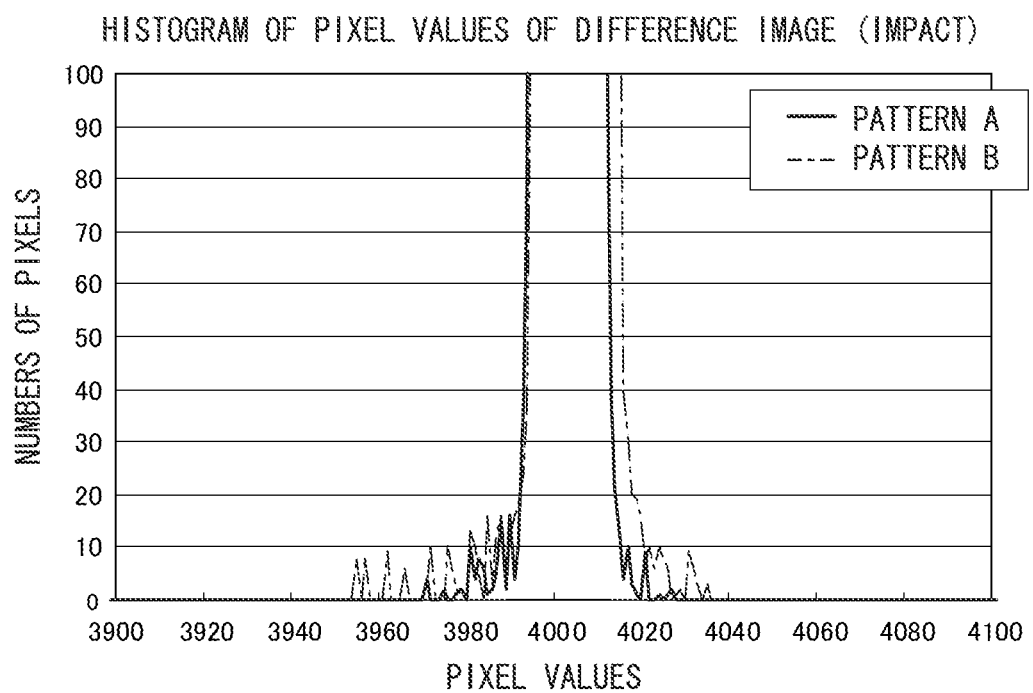

FIGS. 9A and 9B are histograms showing pixel values of pixels in a difference image of an image captured the previous time and an image captured this time in the imaging system 18 pertaining to the first embodiment, with the horizontal axes representing pixel values (QL values) and the vertical axes representing numbers of pixels; FIG. 9A is a drawing showing a case where there is no impact noise and FIG. 9B is a drawing showing a case where there is impact noise. The QL values are values corresponding to the density of the film of the radiographic image obtained by applying radiation, and the QL values may be the values of gradation signals themselves or may be signals obtained by performing predetermined processing on the gradation signals. Furthermore, the pixel values are padded in the entire image by adding 4000 QL, for example, to the pixel value of each pixel in the difference image.

As shown in FIG. 9A, in a case where there is no impact noise in the images captured by the electronic cassette 32, the histogram of the pixel values in the difference image (that is, the differences in the pixel values of corresponding pixels in the image captured the previous time and the image captured this time) shows a regular distribution. On the other hand, as shown in FIG. 9B, in a case where there is impact noise in the images captured by the electronic cassette 32, noise corresponding to the impact noise shown in FIG. 8A occurs at the foot of the peak in the histogram. This is because in a case where there is impact noise in either the image captured the previous time or the image captured this time, the pixel values of the pixels in the difference image become larger in the pixel region corresponding to the section where the impact noise is.

Figure 10:
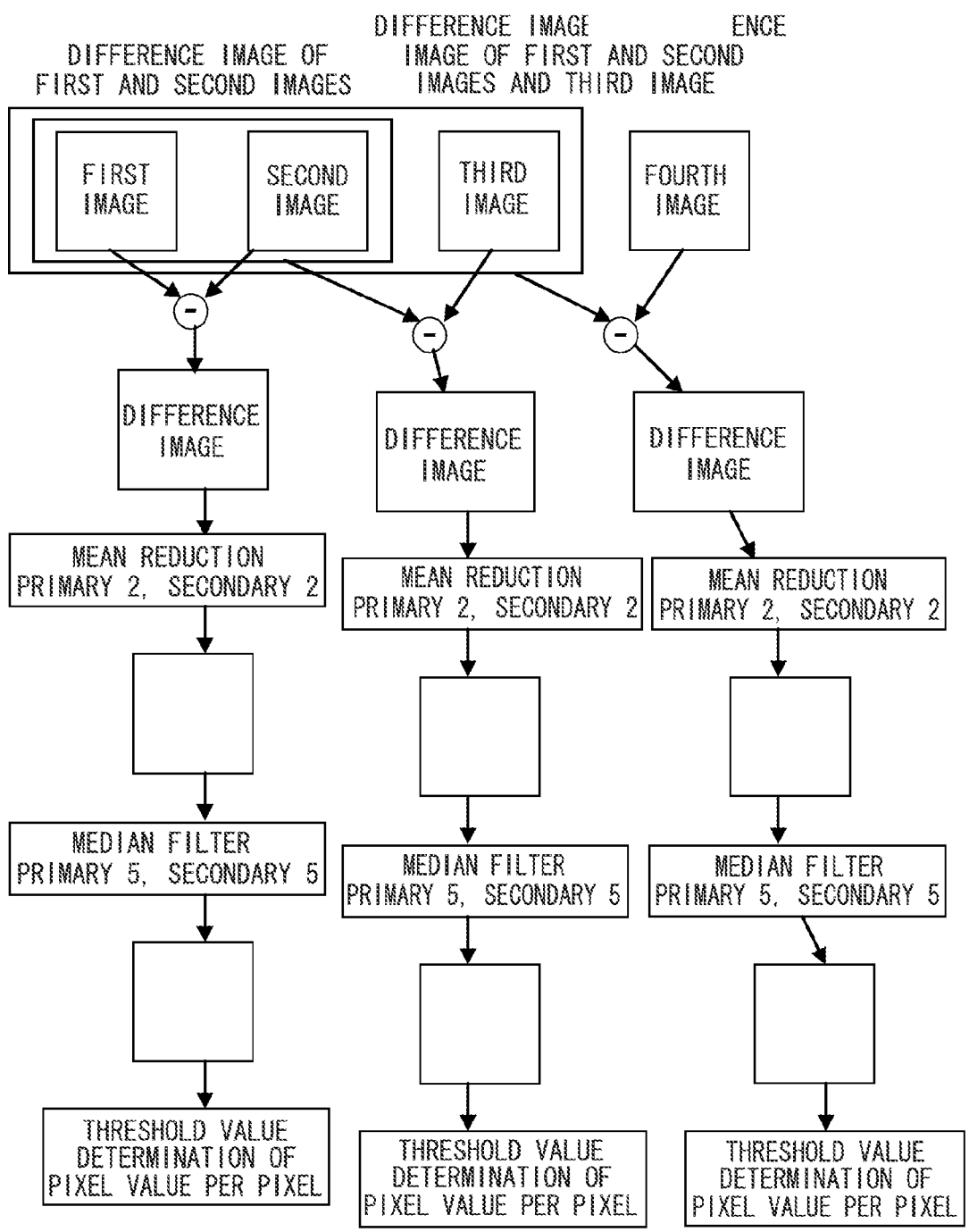
FIG. 10 is a schematic drawing for describing impact noise detection processing in the imaging system pertaining to the embodiments.

FIG. 10 is a schematic drawing for describing impact noise detection processing in the imaging system 18 pertaining to the first embodiment. As shown in FIG. 10, the CPU 104 produces a difference image of the first and second images among the plural images (in the present embodiment, four). The pixel value of each pixel in the difference image is padded by adding 4000 QL, for example, to it. Then, the CPU 104 performs mean reduction processing on the produced difference image. The mean reduction processing is processing that uses a pixel region of a predetermined size (in the present embodiment, a rectangular pixel region comprising two in a primary direction x two in a secondary direction) as a single pixel that takes as its pixel value the mean value of the pixel values of that pixel region. In a case where the mean reduction processing is unnecessary, the mean reduction processing may be omitted.

Furthermore, the CPU 104 performs median filter processing on the reduced image on which the mean reduction processing has been performed (the difference image in the case where the mean reduction processing is not performed). The median filter processing is processing which, when the pixel values of each pixel in a pixel region of a predetermined size (in the present embodiment, a rectangular pixel region comprising five in a main direction×five in a secondary direction) have been arranged in ascending order, uses the pixel value positioned in the center as the pixel value of the pixel in the center of that pixel region. With this median filter processing, point-like noise caused by pixel defects, for example, can be removed from the mean reduction image.

Moreover, the CPU 104 determines, per pixel, whether or not the difference between the pixel value and a reference value (a QL value of 4000) is equal to or greater than a predetermined first threshold value in regard to the median image on which the median filter processing has been performed and counts the total number of pixels that are equal to or greater than the first threshold value. The first threshold value is set to an upper limit value that can be regarded as random noise in the histograms shown in FIG. 8. Furthermore, pixels whose pixel values are equal to or greater than the first threshold value are pixels in which the absolute values of the differences in the pixel values of corresponding pixels in the first image and the second image are large and in which there is the potential for there to be impact noise.

The CPU 104 determines that there is impact noise in the first or second image in a case where the total number of pixels that are equal to or greater than the first threshold value is equal to or greater than a predetermined second threshold value. The second threshold value is set to a numerical value representing an upper limit value with which the total number of pixels that are equal to or greater than the first threshold value can be regarded as random noise. Furthermore, in a case where it is known that there is no impact noise in the first image, it can be determined that there is impact noise in the second image.

In a case where impact noise has not been detected in the first and second images as a result of performing the impact noise detection processing in regard to the first and second images, the CPU 104 performs the impact noise detection processing in regard to the difference image of the first and second images and the third image. And in a case where impact noise has likewise not been detected in the third image, the CPU 104 performs the impact noise detection processing in regard to a difference image of that difference image and the third image and the fourth image. At this time, in a case where impact noise has been detected in any of the first to fourth images at any stage, the CPU 104 determines that impact noise has been detected and cancels the impact noise detection processing. In this way, by producing a difference image of other plural images in which impact noise has not been detected and producing a difference image of this difference image and an image taken as a detection target, error caused by random noise can be reduced.

In the first embodiment, the CPU 104 uses a difference image in the impact noise detection processing, but the CPU 104 is not limited to this and may also use a mean image instead of a difference image in the impact noise detection processing. That is, the CPU 104 may also be configured to perform the impact noise detection processing in regard to the first and second images, perform the impact noise detection processing in regard to a mean image of the first and second images and the third image, and perform the impact noise detection processing in regard to a mean image of the first to third images and the fourth image.

Furthermore, in the first embodiment, in the impact noise detection processing, the CPU 104 uses the first and second images as detection target images and produces a difference image of the first and second images, but the CPU 104 is not limited to this and may also produce a difference image or a mean image of an image already stored in the RAM 108 as an image for offset correction and each of the first to fourth images.

In a case where it has been determined in step S305 that impact noise has not been detected, in step S307 the CPU 104 determines whether or not electromagnetic wave noise has been detected from the received image data.

Figure 11A:
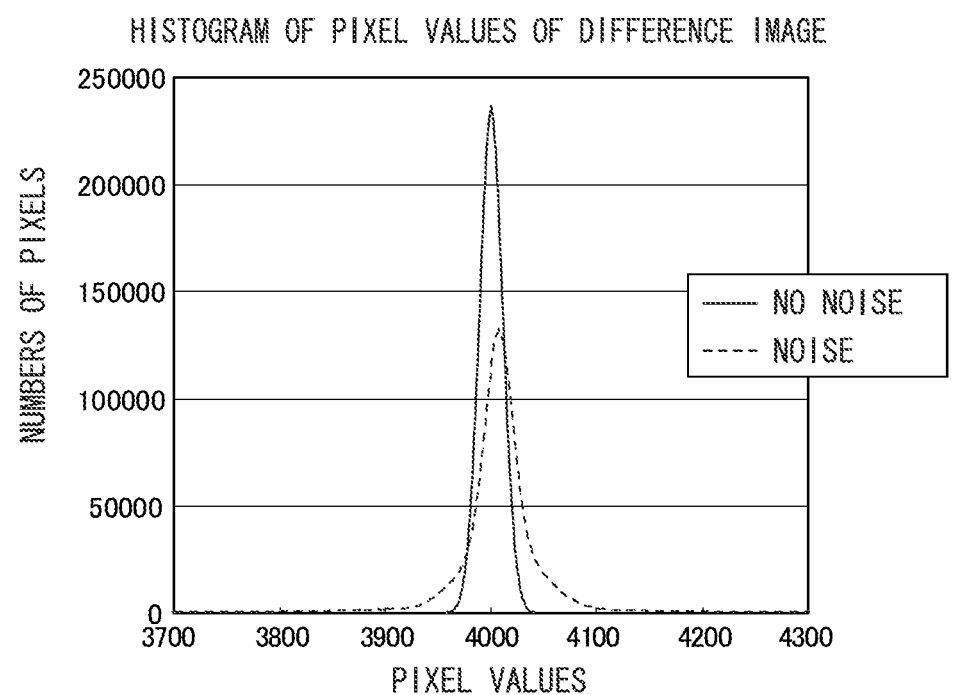
FIG. 11A is a histogram showing pixel values of pixels in a difference image of an image captured the previous time and an image captured this time in the imaging system pertaining to the embodiments, with the horizontal axis representing pixel values (QL values) and the vertical axis representing numbers of pixels.
Figure 11B:
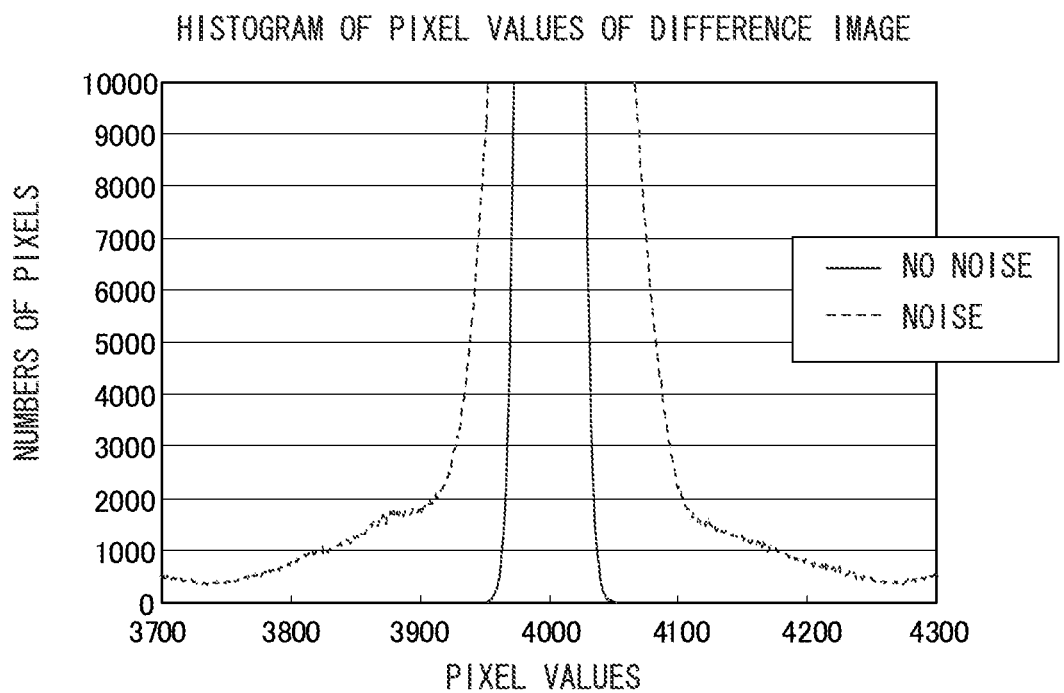
FIG. 11B is a drawing in which the scale of the graph in FIG. 11A has been changed.

FIG. 11A is a histogram showing pixel values of pixels in a difference image of an image captured the previous time and an image captured this time in the imaging system 18 pertaining to the first embodiment, with the horizontal axis representing pixel values (QL values) and the vertical axis representing numbers of pixels, and FIG. 11B is a drawing in which the scale of the graph in FIG. 11A has been changed. The pixel values are padded in the entire image by adding 4000 QL, for example, to the pixel value of each pixel in the difference image.

As shown in FIGS. 11A and 11B, in a case where there is no electromagnetic wave noise in the images that have been captured by the electronic cassette 32, the histogram of the differences in the pixel values shows a regular distribution having a sharp peak. On the other hand, in a case where there is electromagnetic wave noise in the images that have been captured by the electronic cassette 32, the spread of the peak in the histogram differs from the case where there is no electromagnetic wave noise in that the width of the peak becomes wider and the height of the peak becomes lower because, as mentioned above, electromagnetic wave noise is noise that occurs in the entire image. This is because in a case where there is no electromagnetic wave noise in the image captured the previous time but there is electromagnetic wave noise in the image captured this time, the differences in the pixel values of the corresponding pixels in the image captured the previous time and the image captured this time become larger in the entire image, that is, the pixel values of the pixels in the difference image become larger.

Figure 12:
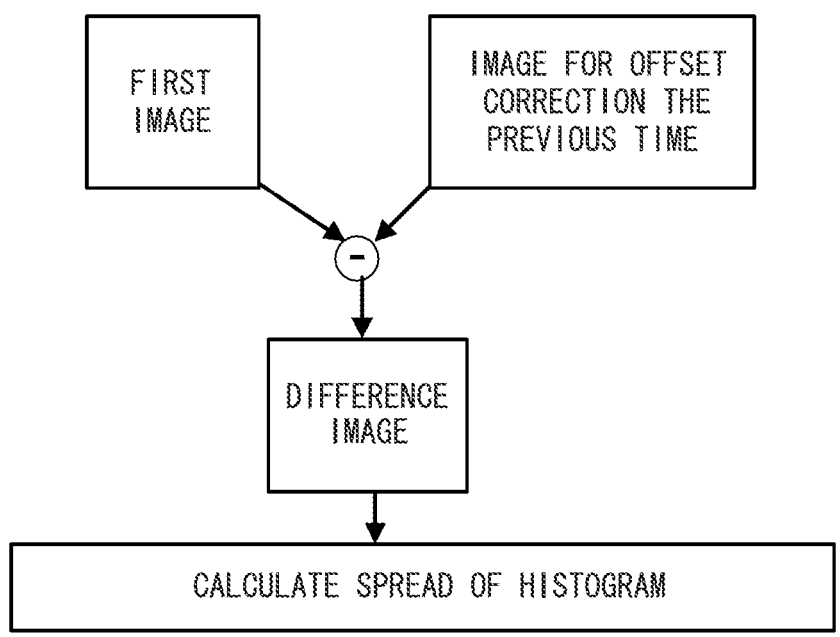
FIG. 12 is a schematic drawing for describing electromagnetic wave noise detection processing in the imaging system pertaining to the embodiments.

FIG. 12 is a schematic drawing for describing electromagnetic wave noise detection processing in the imaging system 18 pertaining to the first embodiment. As shown in FIG. 12, the CPU 104 produces a difference image of an image for offset correction the previous time (an image already stored in the RAM 108 as an image for offset correction) and the first image. The pixel value of each pixel in the difference image is padded by adding 4000 QL, for example, to it. Furthermore, the aforementioned mean reduction processing and median filter processing are performed on the first to fourth images.

Furthermore, the CPU 104 produces, in regard to the produced difference image, a histogram in which the horizontal axis represents differences in pixel values (QL values) and the vertical axis represents numbers of pixels, and derives the spread of the width of the peak in the histogram. Then, the CPU 104 determines whether or not the width of the peak is equal to or greater than a predetermined third threshold value. The third threshold value is set to a numerical value representing an upper limit value with which the width of the peak can be regarded as random noise. In consideration of the fact that the width of the peak in the histogram becomes wider in a case where there is electromagnetic wave noise in the image captured this time, the CPU 104 determines that there is electromagnetic wave noise in the image captured this time in a case where the width of the peak is equal to or greater than the third threshold value.

The CPU 104 performs the electromagnetic wave noise detection processing in regard to the first to fourth images and determines that electromagnetic wave noise has been detected in a case where electromagnetic wave noise has been detected in any of the images.

In a case where there is not an image already stored in the RAM 108 as an image for offset correction, in the electromagnetic wave noise detection processing, the CPU 104 produces a difference image with respect to each of the first to fourth images. In a case where there is electromagnetic wave noise in any of the first to fourth images, by utilizing the fact that the spread of the histogram differs in that image with respect to another image, it can be determined that there is electromagnetic wave noise in the image in which the spread differs with respect to another image.

Furthermore, in the first embodiment, the CPU 104 determines whether or not there is electromagnetic wave noise by determining whether or not the width of the peak in the histogram is equal to or greater than the third threshold value, but the determination method is not limited to this, and the CPU 104 can also make the determination by any of determining whether or not the half width of the peak is equal to or greater than a predetermined value, determining whether or not the height of the peak is equal to or less than a predetermined value, and determining whether or not the ratio of the height of the peak with respect to the half width of the peak is equal to or greater than a predetermined value.

In a case where it has been determined in step S307 that electromagnetic wave noise has not been detected, in step S309 the CPU 104 determines whether or not scatter radiation noise has been detected from the received image data. Here, utilizing the fact that, in a case where scatter radiation of X-rays or the like has been made incident on the electronic cassette 32, the pixel density in the pixel region where the scatter radiation was made incident differs greatly from the pixel density in pixel regions where the scatter radiation was not made incident, the CPU 104 determines whether or not there is scatter radiation noise by detecting whether or not there is a region in which the pixel density greatly differs. The aforementioned mean reduction processing and median filter processing are performed on the first to fourth images.

Figure 13:
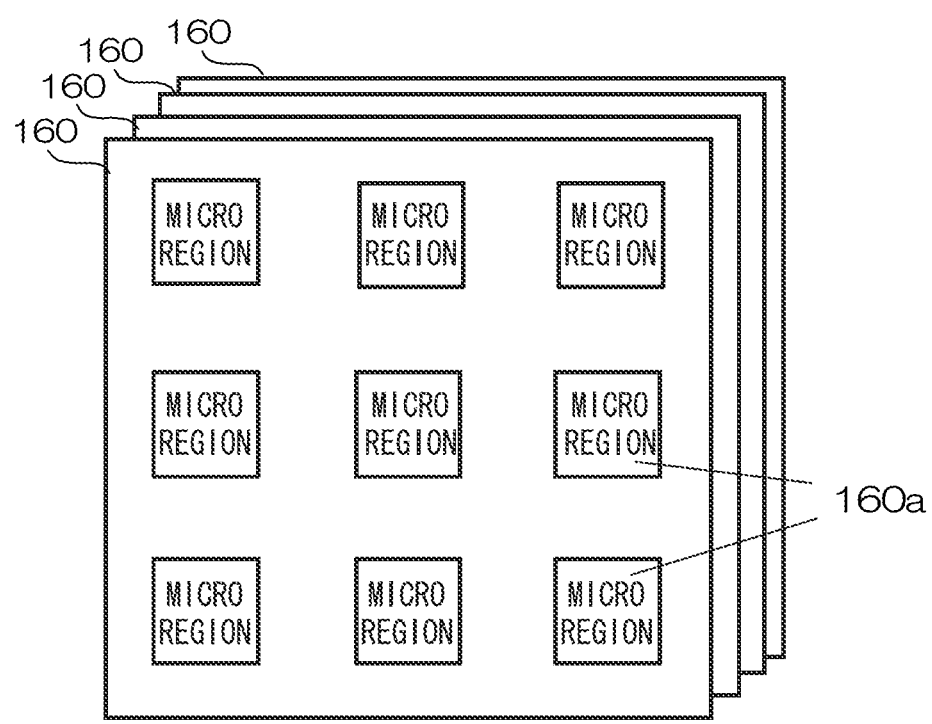
FIG. 13 is a drawing showing an example of detection target regions in the imaging system pertaining to the embodiments.

FIG. 13 is a drawing showing an example of detection target regions 160a in the imaging system 18 pertaining to the first embodiment. As shown in FIG. 13, in each of the first to fourth images 160, plural (in the present embodiment, nine) pixel regions of a predetermined size located in predetermined regions are preset as the detection target regions 160a.

The CPU 104 derives the mean value of the pixel values of the pixels in each of the plural target detection regions 160a in regard to each of the first to fourth images 160 and determines whether or not the derived mean values are equal to or greater than a predetermined fourth threshold value. The fourth threshold value is the numerical value of an upper limit value with which the mean values of the pixel values of the pixels of the target detection regions 160a can be regarded as random noise. Furthermore, the CPU 104 determines that there is scatter radiation noise in the image being taken as the determination target in a case where the mean value of the pixel values in any of the detection target regions 160a is equal to or greater than the fourth threshold value.

The CPU 104 determines that scatter radiation noise has been detected in a case where scatter radiation noise has been detected in any of the first to fourth images.

In a case where it has been determined in step S309 that scatter radiation noise has not been detected, in step S311 the CPU 104 produces a mean image of the first to fourth images as an image for offset correction and stores the produced image for offset in a predetermined region of the RAM 108 to thereby update the image for offset correction.

Furthermore, in a case where it has been determined in step S305 that impact noise has not been detected, or in a case where it has been determined in step S307 that electromagnetic wave noise has not been detected, or in a case where it has been determined in step S309 that scatter radiation noise has not been detected, in step S313 the CPU 104 stands by until a predetermined amount of time (in the present embodiment, 10 minutes) elapses without producing an image for offset correction based on the image data received in step S303, and thereafter the CPU 104 returns to step S301 and again performs the processing of steps S301 to S313. The predetermined amount of time is an amount of time needed until the occurrence of the various types of noise described above settles.

When the radiographer selects the "finished" button on the initial information input screen in step S203, depending on the posture (recumbent position or upright position) of the subject that was input on the initial information input screen, the radiographer either puts the electronic cassette 32 into the holder 152 disposed in the bed 46 and positions the subject in the recumbent position in the imaging position 50 in the space above the bed 46 or puts the electronic cassette 32 into the holder 150 in the rack 45 and has the subject stand in the imaging position 48 in the space in front of the rack 45. Next, the radiographer operates the supporting and moving mechanism 52 to dispose the radiation source 130 of the radiation generator 34 in front of the imaging position.

In step S209, the CPU 104 transmits, to the radiation generator 34 via the wireless communication unit 118, the exposure conditions that were input on the initial information input screen to thereby set the exposure conditions. In response to this, the radiation source control unit 134 prepares for exposure in the received exposure conditions.

In step S211, the CPU 104 transmits, to the electronic cassette 32 via the wireless communication unit 118, instruction information instructing the electronic cassette 32 to start executing imaging implementation processing that implements radiographic imaging. In response to this, the electronic cassette 32 starts executing later-described imaging implementation processing.

In step S213, the CPU 104 transmits, to the radiation generator 34 via the wireless communication unit 118, instruction information instructing the radiation generator 34 to start the exposure. In response to this, the radiation generator 34 generates and emits the radiation X from the radiation source 130 at the tube voltage, tube current, and exposure duration corresponding to the exposure conditions received from the console 42 in accordance with the processing of step S209. In response to this, the electronic cassette 32 performs radiographic imaging by the imaging implementation processing and transmits the subject image data obtained thereby to the console 42 via the wireless communication unit 94.

Therefore, in step S215, the CPU 104 determines whether or not it has received the subject image data from the electronic cassette 32. In a case where it has been determined in step S215 that the CPU 104 has received the subject image data, in step S217 the CPU 104 transmits, to the electronic cassette 32 via the wireless communication unit 118, instruction information instructing the electronic cassette 32 to stop the power supply that was started in step S205. In response to this, the electronic cassette 32 controls the power supply unit 96 to stop the power supply.

In step S219, the CPU 104 executes, with respect to the received subject image data, image processing that performs offset correction by subtracting, per pixel, the image data of the image for offset correction that was updated in S207 and which thereafter performs various types of correction such as switching element and leak current correction and amp offset voltage correction.

In step S221, the CPU 104 stores in the HDD 110 the subject image data on which the image processing has been performed (hereinafter called "corrected image data"). Furthermore, in step S223, the CPU 104 controls the display driver 112 in such a way as to cause the radiographic image represented by the corrected image data to be displayed by the display 100 for checking and so forth. Moreover, in step S225, the CPU 104 transmits the corrected image data to the RIS server 14 via the in-hospital network 16 and thereafter ends the radiographic imaging processing program. The corrected image data that have been transmitted to the RIS server 14 are stored in the database 14A and can be used by a doctor to read the captured radiographic image and make a diagnosis.

As described in detail above, according to the first embodiment, the CPU 104 acquires at least one original image, which is a basis when creating a correction image used in offset correction with respect to an image that has been obtained by imaging, determines whether or not noise from the exterior is superimposed on the original image, and, in a case where it has been determined that noise from the exterior is superimposed on the original image, cancels production of the correction image using the original image on which the noise is superimposed. Because of this, when creating a correction image for offset correction, a correction image with little noise can be easily created while ensuring that a correction image having noise superimposed thereon is not created.

It is not invariably necessary for the processing of steps S305, S307, and S309 to be performed in the aforementioned order, and the processing may also be executed in an arbitrarily switched order. Furthermore, it is not invariably necessary for the processing of steps S305, S307, and S309 to all be executed, and the CPU 104 may also be configured to selectively execute the processing of steps S305, S307, and S309 in accordance with device characteristics and environmental conditions.

Furthermore, when an imaging instruction made by a radiographer has been input while the CPU 104 is performing the offset image update processing, the CPU 104 may also be configured in such a way that the imaging is started after the CPU 104 completes the processing of steps S301 to S313 or in such a way that the CPU 104 cancels the offset image update processing without updating the image for offset correction and uses an image for offset correction that is already stored. In a case where there is an image being captured when an imaging instruction made by a radiographer has been input while the CPU 104 is performing the offset image update processing, the CPU 104 cancels the offset image update processing at the stage when the capture of that image is finished.

Furthermore, in the offset image update processing, the imaging system 18 pertaining to the first embodiment creates an image for offset using plural images that have been obtained by performed imaging plural times, but the imaging system 18 is not limited to this and may also create an image for offset using one image that has been obtained by performing imaging one time. In this case, when the CPU 104 performs the impact noise detection processing in step S305, the CPU 104 uses the image for offset correction that is already stored in the RAM 108 and the one image that has been obtained by imaging.

Furthermore, the imaging system 18 pertaining to the first embodiment performs the offset image update processing just before performing imaging with the electronic cassette 32, but the timing when the offset image update processing is performed is not limited to this, and the offset image update processing can be performed at an arbitrary timing.

Furthermore, the imaging system 18 pertaining to the first embodiment performs the offset image update processing with respect to the electronic cassette 32 that captures radiographic images, but the imaging system 18 is not limited to this and may also perform the offset image update processing with respect to an imaging device that performs imaging with a solid-state image sensor. In this case, the CPU 104 acquires, as the original image, an image that has been captured by the solid-state image sensor without the presence of incident light.

Second Embodiment

A radiographic imaging system 10 pertaining to a second embodiment will be described in detail below using the attached drawings. Like the imaging system 10 pertaining to the first embodiment, the radiographic imaging system 10 pertaining to the second embodiment has the configurations shown in FIG. 1 to FIG. 4. The same reference signs will be assigned to configurations that are the same as those in the first embodiment, and redundant description will be omitted.

When the imaging system 18 of the first embodiment updates the image for offset correction, in a case where there is noise in any of the four images, it does not update the image for offset correction using those four images. In contrast, in a case where there is noise in any of the four images, the imaging system 18 pertaining to the second embodiment uses only the images not affected by noise to produce and update the image for offset correction.

A flow of imaging control processing in the imaging system 18 pertaining to the second embodiment will be described.

First, the CPU 104 performs the processing of step S201 to S205 in the same way as in the first embodiment. Then, in step S207, the CPU 104 performs offset image update processing.

Figure 14:
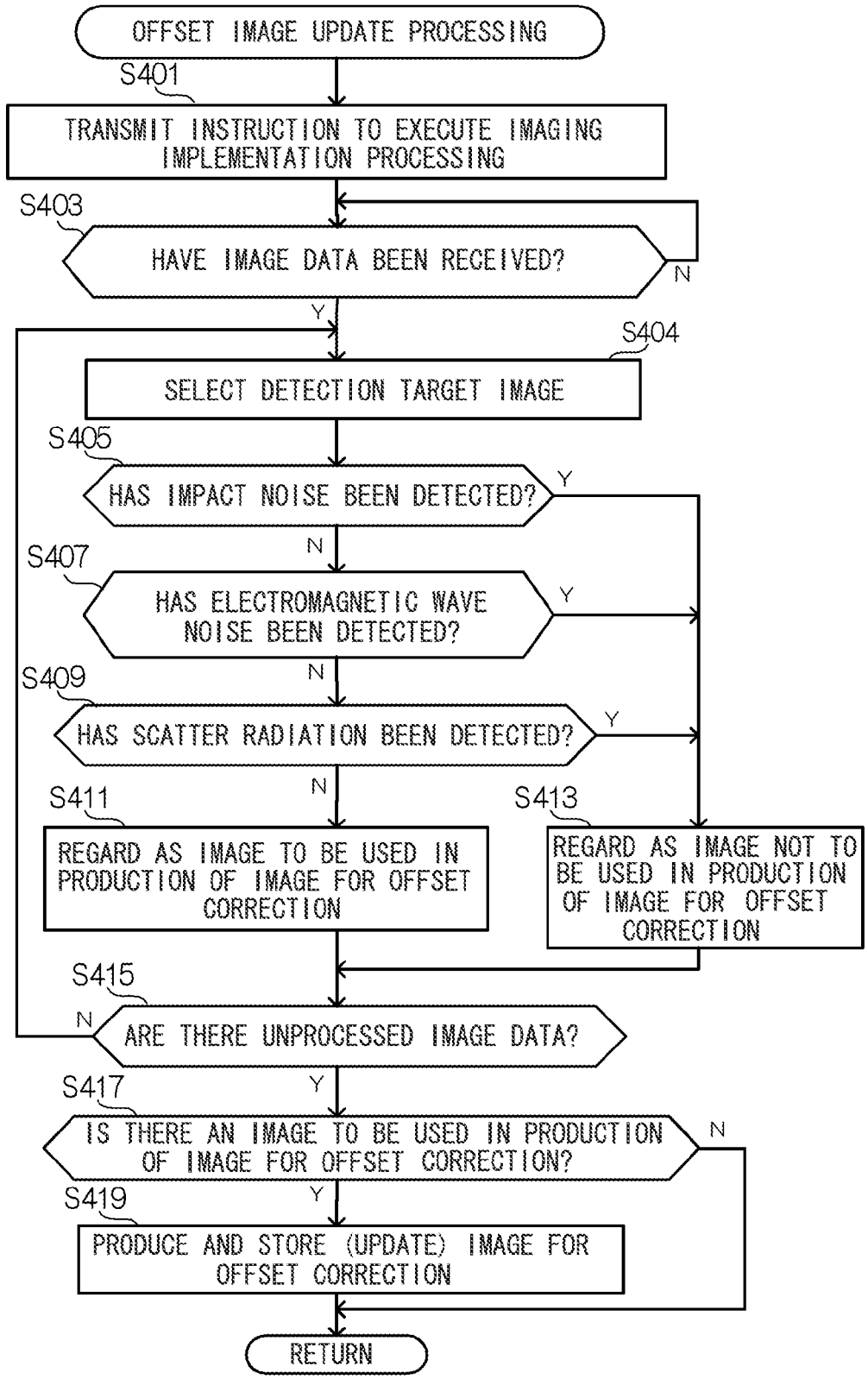
FIG. 14 is a flowchart showing a flow of offset image update processing in the imaging system pertaining to a second embodiment.

FIG. 14 is a flowchart showing a flow of the offset image update processing in the imaging system 18 pertaining to the present embodiment. The offset image update processing is executed by the CPU 104 of the console 42, and a program for performing the offset image update processing is stored beforehand in a predetermined region of the ROM 106.

In steps S401 to S403, the CPU 104 performs the same processing as in steps S301 to S303. In step S404, the CPU 104 selects, from the images represented by the image data received in step S403, an image to serve as a detection target of the various types of noise described above. In steps S405 to S409, the CPU 104 performs the same processing as in steps S305 to S309 in regard to the image selected as the detection target in step 404. Then, in a case where it has been determined in step S409 that scatter radiation noise has not been detected, in step S411 the CPU 104 regards the image serving as the detection target in steps S405 to S409 as an image to be used in the production of an image for offset correction.

When performing the impact noise detection processing in step S405, the CPU 104 uses an image for offset correction that is already stored in the RAM 108 and one image that has been obtained by imaging.

In a case where it has been determined in step S405 that impact noise has been detected, or in a case where it has been determined in step S407 that electromagnetic wave noise has been detected, or in a case where it has been determined in step S409 that scatter radiation noise has been detected, in step S413 the CPU 104 regards the image serving as the detection target in steps S405 to S409 as an image not to be used in the production of an image for offset correction.

In step S415, the CPU 104 determines whether or not there are unprocessed image data, that is, images on which the processing of steps S405 to S413 has not been performed. In a case where it has been determined in step S415 that there are unprocessed image data, the CPU 104 returns to step S405 and performs the processing of steps S405 to S413 in regard to the image represented by the unprocessed image data.

In a case where it has been determined in step S415 that there are no unprocessed image data, in step S417 the CPU 104 determines whether or not there is an image to be used in the production of an image for offset correction, that is, an image that was in step S411 regarded as an image to be used in the production of an image for offset correction.

In a case where it has been determined in step S415 that there is an image to be used in the production of an image for offset correction, in step S419 the CPU 104 updates the image for offset correction by storing, in a predetermined region of the RAM 108 as an image for offset correction, a mean image of the images that were in step S411 regarded as images to be used in the production of an image for offset correction. On the other hand, in a case where it has been determined in step S415 that there is not an image to be used in the production of an image for offset correction, the CPU 104 does not update the image for offset correction.

Then, the CPU 104 performs the processing of steps S209 to S225 in the same way as in the first embodiment and ends the imaging control processing program.

As described in detail above, according to the second embodiment, the CPU 104 creates a correction image using an original image that has been determined as not having noise from the exterior superimposed on it. Because of this, when creating a correction image for offset correction, a correction image with little noise can be easily created while ensuring that a correction image having noise superimposed thereon is not created.

In each of the above embodiments, a case was described where X-rays were applied as the radiation of the present invention, but the present invention is not limited to this and also includes other forms of radiation, such as alpha radiation and gamma radiation, for example.

The present invention has been described above using embodiments, but the technical scope of the present invention is not limited to the scope described in the embodiments. Various changes and improvements can be made to the embodiments without departing from the gist of the invention, and embodiments to which such changes or improvements have been made are included in the technical scope of the present invention.

What is claimed is:

1. A correction image creation device comprising:
   an acquisition unit that acquires at least one original image, which is a basis when creating a correction image used in offset correction with respect to an image that has been obtained by imaging;
   a determination unit that determines whether or not noise, from an exterior, is superimposed on the original image; and
   a cancellation unit that cancels creation of the correction image in a case in which it has been determined by the determination unit that noise from the exterior is superimposed on the original image.

2. The correction image creation device according to claim 1, wherein, in a case in which it has been determined that noise from the exterior is superimposed on the original image, the cancellation unit cancels creation of the correction image that uses the original image on which the noise has been superimposed.

3. The correction image creation device according to claim 2, further comprising a creation unit that creates the correction image, using an original image that has been determined by the determination unit as not having noise from the exterior superimposed on it.

4. The correction image creation device according to claim 1, wherein the correction image creation device acquires, as the original image, a radiographic image that has been captured by an imaging device, which irradiates a subject with radiation from a radiation source and uses a detector to detect radiation that has passed through the subject to thereby capture a radiographic image of the subject, without irradiating a subject with radiation from the radiation source.

5. The correction image creation device according to claim 1, wherein the acquisition unit acquires, as the original image, an image that has been captured by a solid-state image sensor without the presence of incident light.

6. The correction image creation device according to claim 1, wherein the noise is at least one of noise caused by scatter radiation, noise caused by an impact or noise caused by electromagnetic waves.

7. The correction image creation device according to claim 1, wherein the determination unit determines whether or not noise caused by scatter radiation is superimposed, by comparing, against a predetermined threshold value, mean values of pixel values in a plurality of regions in the original image.

8. The correction image creation device according to claim 1, wherein the determination unit determines whether or not noise caused by an impact is superimposed, on the basis of numbers of pixels with respect to differences away from a reference value of a histogram represented by differences in pixel values of corresponding pixels in an image for offset correction that has already been created and an original image, differences in pixel values of corresponding pixels in original images, differences in pixel values of corresponding pixels in a difference image obtained from a plurality of original images on which noise is not superimposed and an original image, or differences in pixel values of corresponding pixels in a mean image of a plurality of original images on which noise is not superimposed and an original image, and numbers of pixels with respect to the differences.

9. The correction image creation device according to claim 1, wherein the determination unit determines whether or not noise caused by electromagnetic waves is superimposed, on the basis of the spread of a histogram represented by differences in pixel values of corresponding pixels in an image for offset correction that has already been created and an original image and numbers of pixels with respect to those differences.

10. The correction image creation device according to claim 1, wherein the determination unit uses, as the original image, an image obtained as a result of noise caused by defective pixels having been removed by a median filter from the original image.

11. A radiographic imaging device comprising:
    an imaging device that irradiates a subject with radiation from a radiation source and uses a detector to detect radiation that has passed through the subject to thereby capture a radiographic image of the subject, and
    a correction image creation device comprising:
       an acquisition unit that acquires at least one original image, which is a basis when creating a correction image used in offset correction with respect to an image that has been obtained by imaging;
       a determination unit that determines whether or not noise, from an exterior, is superimposed on the original image; and
       a cancellation unit that cancels creation of the correction image in a case in which it has been determined by the determination unit that noise from the exterior is superimposed on the original image,
    wherein the correction image creation device acquires, as the original image, a radiographic image that has been captured by the imaging device without irradiating a subject with radiation from the radiation source.

12. The radiographic imaging device according to claim 11, wherein, in a case in which it has been determined that noise from the exterior is superimposed on the original image, the cancellation unit cancels creation of the correction image that uses the original image on which the noise has been superimposed.

13. The radiographic imaging device according to claim 12, further comprising a creation unit that creates the correction image, using an original image that has been determined by the determination unit as not having noise from the exterior superimposed on it.

14. An imaging device comprising:
    the correction image creation device according to claim 5; and
    an imaging device that has a solid-state image sensor.

15. A non-transitory computer readable medium storing a program for causing a computer to function as the correction image creation device according to claim 1.

16. The non-transitory computer readable medium according to claim 15, wherein, in a case in which it has been determined that noise from the exterior is superimposed on the original image, the cancellation unit cancels creation of the correction image that uses the original image on which the noise has been superimposed.

17. The non-transitory computer readable medium according to claim 16, further comprising a creation unit that creates the correction image, using an original image that has been determined by the determination unit as not having noise from the exterior superimposed on it.

18. A correction image creation method comprising:
acquiring at least one original image, which is a basis when creating a correction image used in offset correction with respect to an image that has been obtained by imaging;
determining whether or not noise, from an exterior, is superimposed on the original image; and
cancelling creation of the correction image in a case in which it has been determined that noise from the exterior is superimposed on the original image.

* * * * *